United States Patent
Montgomery et al.

(10) Patent No.: US 11,945,720 B2
(45) Date of Patent: *Apr. 2, 2024

(54) APPARATUS AND METHOD FOR GENERATING NITRIC OXIDE IN CONTROLLED AND ACCURATE AMOUNTS

(71) Applicant: NitricGen, Inc., Fitchburg, WI (US)

(72) Inventors: Frederick John Montgomery, Sun Prairie, WI (US); Cory Casper, Monona, WI (US); Duncan P. L. Bathe, Fitchburg, WI (US); Tye Gribb, Fitchburg, WI (US)

(73) Assignee: NitricGen, Inc., Fitchburg, WI (US)

( * ) Notice: Subject to any disclaimer, the term of this patent is extended or adjusted under 35 U.S.C. 154(b) by 523 days.

This patent is subject to a terminal disclaimer.

(21) Appl. No.: 17/190,841

(22) Filed: Mar. 3, 2021

(65) Prior Publication Data

US 2021/0261416 A1  Aug. 26, 2021

Related U.S. Application Data

(60) Continuation of application No. 17/166,088, filed on Feb. 3, 2021, which is a continuation of application
(Continued)

(51) Int. Cl.
*B01J 19/08* (2006.01)
*A61K 33/00* (2006.01)
(Continued)

(52) U.S. Cl.
CPC ............ *C01B 21/203* (2013.01); *A61K 33/00* (2013.01); *B01D 46/00* (2013.01);
(Continued)

(58) Field of Classification Search
CPC ................... B01J 19/088; B01J 12/002; B01J 2219/0801; B01J 2219/0809;
(Continued)

(56) References Cited

U.S. PATENT DOCUMENTS 4,505,795 A   3/1985  Alamaro
5,354,365 A  10/1994  Youn
(Continued)

FOREIGN PATENT DOCUMENTS

CN   1730115 A   2/2006
CN  101036482 A   9/2007
(Continued)

OTHER PUBLICATIONS

Amendment/Request for Reconsideration After Non-Final Rejection filed on Nov. 28, 2018 in U.S. Appl. No. 15/880,018, pp. 1-9.
(Continued)

*Primary Examiner* — Lessanework Seifu
(74) *Attorney, Agent, or Firm* — Elmore Patent Law Group, P.C.; Joseph C. Zucchero; Carolyn S. Elmore

(57) ABSTRACT

A nitric oxide generator generates nitric oxide from a mixture of nitrogen and oxygen such as air treated by a pulsating electrical discharge. The desired concentration of nitric oxide is obtained by controlling at least one of a frequency of the pulsating electrical discharge and duration of each electrical discharge pulse.

33 Claims, 6 Drawing Sheets

Nitric Oxide Generator Schematic

Related U.S. Application Data

No. 16/837,787, filed on Apr. 1, 2020, now Pat. No. 10,919,768, which is a continuation of application No. 15/887,246, filed on Feb. 2, 2018, now abandoned, which is a division of application No. 15/372,552, filed on Dec. 8, 2016, now Pat. No. 9,896,337, which is a division of application No. 14/347,479, filed as application No. PCT/US2012/058564 on Oct. 3, 2012, now Pat. No. 9,573,110.

(60) Provisional application No. 61/542,400, filed on Oct. 3, 2011.

(51) Int. Cl.
| | |
|---|---|
| B01D 46/00 | (2022.01) |
| B01D 53/02 | (2006.01) |
| B01J 20/04 | (2006.01) |
| B01J 20/08 | (2006.01) |
| B01J 20/10 | (2006.01) |
| B01J 20/20 | (2006.01) |
| B01J 20/22 | (2006.01) |
| B01J 20/28 | (2006.01) |
| C01B 21/20 | (2006.01) |
| C01B 21/32 | (2006.01) |
| H04L 9/30 | (2006.01) |
| H05H 1/46 | (2006.01) |
| H05H 1/50 | (2006.01) |

(52) U.S. Cl.
CPC ......... *B01D 46/0084* (2013.01); *B01D 53/02* (2013.01); *B01J 19/088* (2013.01); *B01J 20/041* (2013.01); *B01J 20/08* (2013.01); *B01J 20/103* (2013.01); *B01J 20/20* (2013.01); *B01J 20/22* (2013.01); *B01J 20/28047* (2013.01); *C01B 21/32* (2013.01); *H04L 9/30* (2013.01); *H05H 1/46* (2013.01); *B01J 2219/0801* (2013.01); *B01J 2219/0809* (2013.01); *B01J 2219/0815* (2013.01); *B01J 2219/0826* (2013.01); *B01J 2219/0852* (2013.01); *B01J 2219/0869* (2013.01); *B01J 2219/0875* (2013.01); *B01J 2219/0883* (2013.01); *B01J 2219/0894* (2013.01); *H05H 1/50* (2013.01)

(58) Field of Classification Search
CPC ........ B01J 2219/0815; B01J 2219/0869; B01J 2219/0883; B01J 2219/0894; C01B 21/203; A61K 33/00
See application file for complete search history.

(56) References Cited

U.S. PATENT DOCUMENTS

| | | | |
|---|---|---|---|
| 5,396,882 | A | 3/1995 | Zapol |
| 5,503,808 | A | 4/1996 | Garbutt et al. |
| 5,558,083 | A | 9/1996 | Bathe et al. |
| 5,692,495 | A | 12/1997 | Sheu |
| 5,827,420 | A | 10/1998 | Shirazi et al. |
| 6,296,827 | B1 | 10/2001 | Castor et al. |
| 6,955,790 | B2 | 10/2005 | Castor et al. |
| 6,972,115 | B1 | 12/2005 | Ballard |
| 7,494,574 | B2 | 2/2009 | Kong et al. |
| 8,574,531 | B2 | 11/2013 | Miller et al. |
| 9,573,110 | B2 | 2/2017 | Montgomery et al. |
| 2001/0031230 | A1 | 10/2001 | Castor et al. |
| 2004/0028753 | A1 | 2/2004 | Hedenstierna et al. |
| 2004/0241339 | A1 | 12/2004 | Anazawa et al. |
| 2005/0061785 | A1 | 3/2005 | Schroder et al. |
| 2005/0218007 | A1 | 10/2005 | Pekshev et al. |
| 2006/0172018 | A1 | 8/2006 | Fine et al. |
| 2006/0276844 | A1 | 12/2006 | Alon et al. |
| 2007/0190184 | A1 | 8/2007 | Montgomery et al. |
| 2009/0136829 | A1 | 5/2009 | Huang et al. |
| 2009/0317310 | A1 | 12/2009 | Coates et al. |
| 2010/0106265 | A1 | 4/2010 | Ebrom et al. |
| 2011/0185895 | A1 | 8/2011 | Freen |
| 2012/0296265 | A1 | 11/2012 | Dobrynin |
| 2012/0318722 | A1 | 12/2012 | Guess |
| 2017/0296836 | A1 | 10/2017 | Dobrynin et al. |
| 2018/0221619 | A1 | 8/2018 | Zapol et al. |

FOREIGN PATENT DOCUMENTS

| | | |
|---|---|---|
| EP | 2151554 A1 | 2/2010 |
| GB | 190627006 A | 11/1907 |
| WO | 9507610 A1 | 3/1995 |
| WO | 2013052548 A2 | 4/2013 |
| WO | 2013181179 A1 | 12/2013 |
| WO | 2014143842 A1 | 9/2014 |

OTHER PUBLICATIONS

Applicant Initiated Interview Summary dated Oct. 30, 2018 in U.S. Appl. No. 15/880,018.
European Search Report, Application No. 12838012.8; dated Nov. 30, 2015.
https://en.wikipedia.org/wiki/Mass_flow_controller. Retrieved from the internet on Oct. 28, 2019.
International Search Authority, International Search Report and The Written Opinion of PCT/US2012/058564; filed Oct. 3, 2012.
Non-Final Office Action dated Aug. 31, 2018 in U.S. Appl. No. 15/880,018.
Hu, et al., Study on Production of Inhaled Nitric Oxide for Medical Applications by Pulsed Discharge, IEEE Transactions on Plasma Science, vol. 35(3), Jun. 2007.
Namihira, et al., "Production of Nitric Oxide Using a Pulsed Arc Discharge," IEEE Transactions on Plasma Science, 30(5): 1993-1998 (2002).
https://de.wikipedia.org/wiki/Stromventil, obtained on Sep. 9, 2019 (translated).
Wikipedia article "Variable capacitor".
Arjunan, K. P., "Plasma Produced Reactive Oxygen and Nitrogen species in Angiogenesis", PhD thesis, May 2011.
Beanland, M., et al., "Pre-insertion resistors in high voltage capacitor bank switching", Western Protective Relay Conference, Spokane WA. Oct. 19-21, 2004.
Dobrynin, D., et al., "Direct and controllable nitric oxide delivery into biological media and living cells by a pin-to-hole spark discharge (PHO) plasma", J. Phys. D: Appl. Phys., 44, 10 pgs.
Kuo, S. P., et al., "Air plasma for medical applications", J Biomed Sci and Eng., 5, 2012, 481-495.
Namihira, T., et al., "Production of Nitric Monoxide Using Pulsed Discharges for a Medical Application", IEEE Transactions on Plasma Science, 28(1), http://hdl.handle.net/2298/3462, 109-114.
Namihira, T., et al., "Temperature and Nitric Oxide Generation in a Pulsed Arc Discharge Plasma", Plasma Sci. Technol., 9(6), 747-751.
Sakai, S., "Nitric Oxide Generator Based on Pulsed Arc Discharge", Acta Phys. Polonica A, 115(6), 1104-1106.

Figure 1 Nitric Oxide Reactor Chamber

Figure 2 Nitric Oxide Generator Schematic

Figure 3 Electric Discharge Drive Circuit

APPARATUS AND METHOD FOR GENERATING NITRIC OXIDE IN CONTROLLED AND ACCURATE AMOUNTS

RELATED APPLICATIONS

This application is a continuation of U.S. application Ser. No. 17/166,088, filed on Feb. 3, 2021, which is a continuation of U.S. application Ser. No. 16/837,787, filed on Apr. 1, 2020 (now U.S. Pat. No. 10,919,768, issued Feb. 16, 2021), which is a continuation of U.S. application Ser. No. 15/887,246, filed Feb. 2, 2018 (Abandoned), which is a divisional of U.S. application Ser. No. 15/372,552, filed Dec. 8, 2016 (now U.S. Pat. No. 9,896,337, issued Feb. 20, 2018), which is a divisional of U.S. application Ser. No. 14/347,479, filed Mar. 26, 2014 (now U.S. Pat. No. 9,573,110, issued Feb. 21, 2017), which is a US National stage entry of International Application No. PCT/US2012/058564, which designated the United States and was filed on Oct. 3, 2012, published in English, which claims the benefit of U.S. Provisional Application No. 61/542,400, filed on Oct. 3, 2011. The entire teachings of the above applications are incorporated herein by reference.

BACKGROUND OF THE INVENTION

This invention discloses a method and apparatus for the production of nitric oxide (NO) in controlled and accurate amounts, with low levels of impurities by controlling electric discharges between two electrodes in an oxygen nitrogen gas mixture.

Nitric oxide is known to have many applications in biological systems of both plants and animals.

In plants it is known that modifying the local atmospheric concentration of nitric oxide can stimulate a number of beneficial effects including, improved growth (U.S. Pat. No. 6,242,384), reduction in seed dormancy (Bethke, 2006 and Sarath, 2006), protection from fungal infections and disease (Lazar, 2008 and Hong, 2007) and preservation of cut flowers and fruit (U.S. Pat. Nos. 6,451,363 and 6,720,017).

In medical applications, gaseous nitric oxide administered to the patient is known to have multiple applications as disclosed in the following examples.

Anti-microbial: Nitric oxide has been demonstrated to reduce bacterial infections as shown during in-vitro testing (Ghaffari, 2006) and in clinical applications such as skin tissue infections (Ghaffari, 2007) and cystic fibrosis lung infections (Sagel, 2009).

Wound Healing: Nitric oxide has been demonstrated to improve healing times in both sterile and infected wounds (Shekhter, 2005).

Hemoglobinopathy: (U.S. Pat. No. 5,885,621) with application in sickle cell disease, where nitric oxide significantly reduced pain associated with vaso-occlusive crisis in sickle cell patients as compared to placebo (Head, 2010).

Selective pulmonary vasodilatation: (U.S. Pat. No. 5,485,827) with application in hypoxic respiratory failure of the newborn, where nitric oxide therapy selectively dilates the pulmonary vasculature and improves oxygenation, with no negative impact on systemic blood pressure (Clark, 2000).

Anti-inflammatory: (U.S. Pat. No. 6,656,452) with application in reducing ischemia reperfusion injury and the infarct size after myocardial infarction (Liu, 2007).

It is clear that with all these potential commercial applications that make use of the biological effects of nitric oxide, there needs to be an apparatus to deliver nitric oxide in an accurate and controlled amount that is reliable and efficient.

One issue that has to be taken into account when considering a method of nitric oxide delivery is that of nitrogen dioxide ($NO_2$) generation. Nitric oxide, when in the presence of oxygen, reacts to form nitrogen dioxide, which is am irritant to biological systems. To resolve this issue, there are two main approaches for generating and then controlling the delivery of nitric oxide to biological systems. A first approach is to produce nitric oxide from chemical precursors, for example, through the oxidation of ammonia and to store the nitric oxide with a diluent gas that does not contain oxygen (the gas used is normally nitrogen) in a high pressure cylinder. As the nitric oxide is needed, a delivery system (for example, a metering valve) controls the flow of nitric oxide gas from the cylinder to provide the amount of nitric oxide needed for any given application. The benefit of this approach is that it is relatively easy to control the amount of nitric oxide gas needed for a specific application and the purity of the nitric oxide can be ensured by a well controlled production process in a centralized production manufacturing location. The main problem with this approach is that the cylinders of compressed nitric oxide gas are large and heavy and are logistically difficult and expensive to ship from the centralized location to the site of application.

A second approach is to generate the nitric oxide gas in-situ from room air, using a controlled electric discharge to ionize the gas at a locally higher temperature to form a plasma, where oxygen and nitrogen in the air break down and reform to produce nitric oxide. This nitric oxide generating approach has the advantage that it does not have the logistical problems of the gas cylinder storage method. It is however, more difficult to accurately and controllably produce the required amounts of nitric oxide with the required purity.

Before providing a description of the invention an overview of background art will be described.

The use of electric discharges to produce nitric oxide in a plasma reaction has a long history, a good summary of which is included in U.S. Pat. No. 4,287,040 by Alamaro. This early prior art was focused on the bulk production of nitric oxide as an intermediary to the production of nitrogen based fertilizers and describes a process that is not concerned with the accuracy, purity and safety of the nitric oxide generated.

U.S. Pat. No. 5,396,882 (Zapol) was the first to disclose a system for producing nitric oxide by electric discharge for use in medicine. In this method, there is an electrically insulated reaction chamber where a high voltage circuit is used to induce an electric arc discharge between two electrodes that are separated by an air gap to produce nitric oxide. The patent discloses gas filters in the inlet conduit to the reaction chamber to remove liquid droplets or solid particles from entering the reaction chamber, and a soda lime filter in the outlet conduit of the reactor chamber for removing impurities such as nitrogen dioxide that may be formed in the plasma along with the nitric oxide. Also described is a gas analyzer such as a chemiluminescence analyzer for measuring the amount of nitric oxide produced. The high voltage circuit includes a step up transformer, which takes standard AC power of 110V and 60 Hz (230V and 50 Hz in Europe) in the primary coil, and steps up the voltage so that the peak voltage is sufficient to induce an electric arc across the electrode air gap. There is a capacitor on the secondary side of the transformer, which is charged up to the breakdown voltage, and subsequently discharged across the gap when the breakdown voltage is reached. The current to the primary side of the transformer is regulated by an autotransformer (Variac), which controls the power to the capacitor and hence on to the electric arc discharge. The current from the capacitor is not controlled once break down voltage has occurred, and this results in an arc discharge which is quick and intense with a high current and high gas temperatures. The system describes producing nitric oxide continuously and controls the amount generated by controlling the current to the transformer, it also describes controlling the amount of diluting gas flow to provide the desired concentration.

There are a number of problems with this type of system which include: electric arc discharges cause high current at high temperatures which cause vaporization of the electrode material which leads to excessive wear of the electrodes. Electrode wear is a function of the intensity of the discharge across the electrodes, which translates into the higher the current the higher the electrode wear. The high temperature can also result in higher levels of nitrogen dioxide being formed, which is not desired in a number of biological applications. In addition, due to the electrode wear, the amount of nitric oxide generated in this system is not accurately predictable over periods of time and it requires a nitric oxide gas analyzer to ensure the expected amount of nitric oxide is being generated accurately. A gas analyzer adds expense, bulk and requires the user to calibrate it prior to use, which makes it undesirable for an optimum nitric oxide generation system. The patent discloses a filter for removing nitrogen dioxide from the nitric oxide gas mixture. However the soda lime filter material disclosed has a finite life, and if it is not changed when the life of the filter material is exhausted, the system would allow the nitrogen dioxide to be delivered to the biological system, and this could result in harm to the biological system.

In EP 0719159 (Jacobson), the problem of high energy arc discharges eroding the electrodes was addressed by disclosing a method of controlling the current across the air gap to a low level to produce a "glow discharge" to produce nitric oxide. The invention described multiple ways of initiating the glow discharge such as; using a separate high voltage spark circuit, reducing the pressure in the chamber or initially bringing the two electrodes closer together to initiate the spark. Once the glow discharge was established it was continuously maintained. To control the nitric oxide concentration to be delivered to the biological system the nitric oxide output was diluted with additional gas flow. The disadvantages of this approach are that there is a limited range of current that allows a glow discharge to be formed, and once formed the glow discharge needs to be continuously maintained. This limits the controllable range of the nitric oxide that can be produced. The required nitric oxide concentration to the biological system is achieved through diluting the nitric oxide flow from the reactor chamber with an additional diluting gas flow. However, this means both the gas flow rate and nitric oxide concentration cannot be controlled independently. If lower concentrations of nitric oxide at low gas flow rates are required, then a large portion of the nitric oxide generated is discarded resulting in low efficiency of operation and an additional apparatus associated with safely disposing of the unused nitric oxide gas flow.

U.S. Pat. Nos. 6,296,827 & 6,955,790 (Castor, et al.) disclose an alternative approach to avoiding electrode wear due to high energy arc discharges. These patents disclose an apparatus where a dielectric barrier material covers one of the electrodes and a corona discharge is produced in high frequency discharge pulses to avoid electrode wear. The reactor chamber has to be operated between 400° C. and 800° C. so the non-thermal plasma generates nitric oxide instead of nitrogen dioxide ($NO_2$). The device also discloses the use of a catalyst operated at an elevated temperature to convert any $NO_2$ formed to nitric oxide. The temperature in the reactor is kept below 800° C. to avoid electrode erosion caused by oxygen radicals and above 400° C. to avoid $NO_2$ being formed instead of nitric oxide. The apparatus disclosed that the nitric oxide gas flow is diluted by additional gas to produce the desired concentration of nitric oxide that is needed clinically. The disadvantage of this apparatus is that it requires extra electrical power to heat the gas to 400° C. to 800° C. and then requires the gas to be actively cooled after the reactor chamber before it can be used clinically. This significantly increases the power and complexity of the apparatus. It also has the same problem as EP 0719159, in that it provides a limited controllable range of nitric oxide being produced, and also relies on gas dilution to produce the desired nitric oxide concentration. Therefore it has the same limitation as described in EP 0719159 in that in some applications, it will result in unwanted nitric oxide gas flow that will need to be discarded resulting in inefficient operation and the need for additional apparatus for the safe disposal of the unused nitric oxide.

U.S. Pat. No. 7,498,000 (Pekshev, et al.) discloses a device for forming a nitric oxide containing gas flow using a continuous stationary DC arc discharge. The arc discharge is maintained at a constant voltage level of approximately 120V at 2.3 A, which maintains an arc temperature of 3500° K to 4000° K. The gas flow is then quenched in a water ethanol cooled chamber where it is rapidly cooled to approximately 1000° K to fix the nitric oxide that was generated in the arc discharge, it then goes on to a further cooling area where it is cooled to a temperature of 150° C. before it exits the outlet. The arc discharge is initiated with a high voltage spark discharge from a 5 kV circuit, and uses a stabilization electrode to maintain the arc discharge. The nitric oxide gas concentration at the apparatus outlet is shown in FIG. 14 as 4,000 ppm nitric oxide, and the concentration is shown to decrease as a function of the distance from the outlet, dropping to about 500 ppm nitric oxide at a distance of 200 mm. This drop in nitric oxide concentration is due to the gas mixing with ambient air, and means a large part of the nitric oxide generated never gets to the intended biological target. It also means the user has to be very careful about the distance of the apparatus outlet to the biological target so the intended nitric oxide concentration is delivered correctly. The apparatus disclosed has the same problems as previous art in that the amount of nitric oxide generated is not well controlled and relies on wasteful dilution of the nitric oxide prior to delivery to the biological target. In addition there is no effort made to remove harmful $NO_2$ that will also be formed in the arc discharge.

The prior art have the following disadvantages:
1) The prior art does not disclose apparatus that can control the amount of nitric oxide over a wide range of gas flows and nitric oxide concentrations so that the device can be used for multiple distinct dosing regimens depending on the target application.
2) The prior art does not disclose apparatus that allows for a wide range of nitric oxide outputs without requiring additional gas flow dilution. This results in excess nitric oxide generation that has to be safely disposed of, causing extra cost and complexity.
3) The prior art that uses high voltage electric arc discharges to generate nitric oxide has high electrode wear due to electrode vaporization caused by the intense electric arc discharges.
4) The prior art that uses corona discharges require high reaction chamber temperatures to be maintained that needs additional power, and then require gas cooling systems to bring the gas flow back down to acceptable temperature levels prior to administration, thus adding to the cost, complexity and poor efficiency of the system.

5) None of the prior art provides a simple way of monitoring the correct functioning of the arc discharge so the amount of nitric oxide generated can be accurately predicted.

6) None of the prior art discloses a consumable filter for removing $NO_2$ and other adulterants from the nitric oxide gas flow that when consumed, can provide the nitric oxide apparatus with a means of alerting the user that it needs to be replaced.

SUMMARY OF THE INVENTION

The present inventors have identified the above disadvantages and the invention described in this specification provides solutions to the above disadvantages and discloses methods and apparatus for the accurate production of nitric oxide over a wide range of output in a reliable and efficient way.

A feature of at least one embodiment of the invention is to provide an improved apparatus and method for the generation of nitric oxide using a gas plasma produced by electric discharges across two electrodes, which overcome the disadvantages previously described in the prior art. In solving the disadvantages of the previously described prior art, the invention makes it particularly appropriate for treating biological systems with nitric oxide that is both accurately controlled and that ensures low levels of impurities.

At least one embodiment of the invention includes a reactor chamber with a gas inlet for a gas flow of air, or other oxygen and nitrogen containing gases, to enter the reactor chamber, two electrodes separated by a gap, an electronic control circuit connected to the electrodes to generate an electric discharge across the gap to produce nitric oxide, and an outlet for the nitric oxide containing gas mixture to exit the chamber.

One embodiment of the invention produces nitric oxide in accurately controlled amounts over a wide range of gas flow rates and nitric oxide concentrations by controlling one or both of the pulse frequency (number of complete electric discharges per second) and/or the pulse duration (length of each complete electric discharge) of electric pulse discharges across the electrode gap. The amount of nitric oxide generated is proportional to both the frequency and the duration of the electric pulse discharges and so either one by itself of in combination with the two can provide a wide control range of nitric oxide generation.

In one embodiment of the invention, the electronic control circuit starts each electric discharge pulse with a short phase of high voltage to initially ionize the gases and to allow electric current to start flowing across the electrode gap, this is then followed by a second phase of the pulse, which is of a lower voltage and current. In one embodiment of the invention, the first high voltage phase of the pulse is kept to a small period of time that is just long enough to initially ionize the gases between the electrodes and to allow electric current to flow in the electrode gap. In the second phase of the pulse the voltage and the current is reduced to lower values and this phase corresponds to the adjustable duration phase of the electric pulse discharge. In one embodiment of the invention the apparatus is designed so that the majority of the nitric oxide is generated during the more efficient second phase. There are a number of stable voltage and current combinations that can be used in this second phase of discharge and they have different advantages and disadvantages. This type of electric discharge with intermittent pulse operation with controlled frequency and/or duration at a controlled, predominantly low current provides benefits including:

It produces nitric oxide efficiently by only producing the amount of nitric oxide needed for the application without the need for additional diluent gases.

It produces nitric oxide without significant increase in the temperature of the gases going to the biological system and therefore does not need cooling apparatus.

It significantly reduces electrode wear due to vaporization of the electrode because the average electric current is low.

The low current and intermittent pulse electric discharge generates nitric oxide efficiently without generating high levels of $NO_2$.

Another desired feature of at least one embodiment of the invention is to generate nitric oxide more efficiently with lower power consumption. One novel approach used in one embodiment of the invention to improve the nitric oxide generating efficiency is to provide a magnetic field across the electrode gap. This can be achieved by using either electric coils or permanent magnets to provide the magnetic field across the electrode gap. With a magnetic field crossing perpendicular to the gap, an increase in the quantity of nitric oxide generated of up to 45% for the same electric discharge pulse settings was shown. Specific examples of improved efficiency will be given in the detailed description section of the invention.

Another feature of a nitric oxide generation apparatus useful with biological systems is that undesirable changes in the amount of nitric oxide generated may be anticipated to alert the user to the alarm condition. The alarm can be an audio or visual indicator or an external signal so that corrective action can be taken such as getting a replacement nitric oxide generation system. Examples of the typical kind of failures that can cause the nitric oxide generation apparatus to stop functioning or to only produce partial nitric oxide output are as follows:

The electrode gap becomes larger due to wear over time.

The electrical insulation in the high voltage circuit breaks down and causes the electric charge to leak to ground without passing through the electrodes.

A component failure in electronic control circuit due to electromagnetic pulses from the electric discharges.

A power supply failure to the electronic control circuit.

The gas flow through the reaction chamber is higher or lower than desired.

In the prior art this was achieved with a nitric oxide gas monitor, however the problem with this approach is that gas monitors are complex, bulky and require periodic calibration by the user adding to the overall complexity of use. In one embodiment of the invention the need for gas monitoring is alleviated by independently monitoring the pulse frequency and pulse duration of the electric discharge in the reaction chamber and having a flow sensor to redundantly monitor the gas flow through the reaction chamber. The basic physics of gas plasma reactions is well understood and if there is an independent sensor that monitors the frequency and the duration of the electric discharge pulse then the correct amount of nitric oxide being generated can be accurately predicted. A number of different sensing technologies can be used to independently monitor the electric discharge.

The discharge monitor sensor can be a photodiode in optical connection to the reaction chamber, which monitors the light generated by the electric discharge. The frequency and duration of the light emitted by the electric discharge pulse and detected by the photodiode will be in proportion to the electric discharge pulse. If there is not a discharge pulse, or if it is intermittent, or a different duration, then the photodiode will detect the malfunction and cause an alarm. In one embodiment, the photodiode may be used to provide feedback correction of the electric discharge pulse to ensure consistent arc length and duration.

The discharge monitor sensor can also be an electric current or voltage sensor that monitors the electric current or voltage across the electrode gap when the pulse occurs to determine the frequency and duration.

The discharge monitor sensor could also be a field effect (Hall Effect) transducer that monitors the magnetic field or flux across the electrode gap when the discharge pulse occurs. The transducer can monitor magnetic field/flux that occurs when an electrical discharge pulse is taking place, and its frequency and duration can be monitored and an alarm generated if a malfunction has occurred.

As well as monitoring the electric discharge is producing the correct amount of nitric oxide, the apparatus may also monitors the air flow rate through the reaction chamber with a gas flow sensor. This ensures that the nitric oxide generated by the apparatus is being delivered from the reaction chamber to the biological system at the require flow rate. If the apparatus is set to deliver a specific gas flow rate at a specific nitric oxide concentration, then the combination of the discharge monitor sensor (to determine the amount of nitric oxide being produced) and the gas flow sensor can be used to ensure the nitric oxide concentration is correct to the set level and provide an alarm if incorrect.

Another requirement is that adulterants such as $NO_2$ are kept at acceptable level s when nitric oxide is being delivered to a biological system. Previous prior art have described filters that can be attached to the outlet of the device that can either convert $NO_2$ to nitric oxide or to remove $NO_2$ from the gas stream. The problem with these filters is they have a finite life that is dependent on how much $NO_2$ they are exposed to. If the user does not replace them when they are consumed, then the biological system may be unintentionally exposed to levels of adulterants that can cause harm to the biological system. One embodiment of the invention provides a novel way to ensure that the user is informed when the filter is approaching its expiry limit and when it is fully expired. It may also stop delivering nitric oxide when the filter is expired if the biological system is especially sensitive to the levels of $NO_2$ that may be present without the filter.

One embodiment of the nitric oxide generation apparatus has a machine readable and programmable interface between the apparatus and the filter and this interface communicates with a non-volatile programmable and readable memory device located in the filter assembly. The filter memory device can be programmed during manufacturing with a number of parameters that can be read by the nitric oxide generation apparatus when it is attached to the device. These parameters can include the capacity of the filter in hours, or in hours per quantity of nitric oxide ($NO_2$ is produced in amounts proportional to the amount of nitric oxide generated) that is being delivered, and that the filter has been shown to remove adulterants effectively. As the filter is consumed, the filter programmable memory is updated with data that allows the remaining capacity of the filter to be determined by the nitric oxide generation apparatus. For instance, the filter memory can be updated periodically with the new current filter capacity based on the original filter capacity and the amount of time the nitric oxide generation apparatus has been in use at a particular nitric oxide setting. This means the filter always has an accurate representation of the remaining capacity programmed into the filter memory. This has the advantage that a completely used up filter can not be accidentally put on the same or even a different device at some point in the future resulting in the biological system getting exposed to high levels of adulterants. There are a number of programmable memory technologies that could be used for this function. Two examples include EEPROM (electrically erasable programmable read only memory) and FLASH, which was developed from EEPROM and must be erased in fairly large blocks before these can be rewritten with new data. One embodiment of this invention uses an EEPROM with a serial interface for reading and reprogramming the memory. Another embodiment uses a micro-controller which includes EEPROM and FLASH memory and communicates to the nitric oxide generator device by a serial interface. However, the invention is not meant to be limited to these specific types of memory technology and could equally apply to other types of programmable memory.

As well as the filter life/capacity parameter there can also be other useful parameters programmed into the filter that can greatly simplify the setup and use of the apparatus. One set of parameters that could also be programmed into the filter memory can be related to the dosing information for the particular biological system treatment regime. This could include the dose setting in nmoles/sec, ppm at the desired flow rate through the reaction chamber to the nitric oxide applicator, and the treatment time for which the dose should be applied. The filter (with memory) can be packaged and attached to the nitric oxide applicator for a particular application so a user can simply open the applicator package and connect it to the nitric oxide generation apparatus. All the dose settings would be read automatically from the filter memory when it is attached to update the apparatus settings prior to use. Each application could have a custom applicator that is optimized for that biological system with the correct sized filter for the required dose and duration. The dose parameters can in some cases be set to zero if the biological application is to be used in a blinded placebo controlled study where some subjects would get nitric oxide and some would only get a flow of gas. In these cases the apparatus display would not display the actual dose setting but would be blank or loaded with a dummy setting so the user would not know which dosing regimen they were on. For added protection against un-blinding a study, these dose parameters could be encrypted at the factory and then de-encrypted by the device when the filter was connected. The encryption would prevent users from effectively reading the filter dose parameters with a memory programming tool prior to use. This means a single nitric oxide generating apparatus can have wide spread application with no changes to the device itself, with only the nitric oxide applicators being customized for the specific biological system.

Another set of parameters that can be programmed into the filter memory that are specific to individual biological systems can revolve around the proper functions of the apparatus. These parameters can set what alarms will be present for different detected conditions, and whether they will involve audible and/or visual alarms and/or if the device should stop generating nitric oxide and stop gas flow through the reaction chamber when these conditions occur. The conditions that can be detected by the apparatus can include the following possible fault conditions:

1) The flow through the reaction chamber is lower or higher than the set value.
2) The $NO_2$ filter has no hours/capacity left or is approaching that condition.
3) The electric discharge pulses are not at the desired frequency or duration for the dose setting resulting in either too high or too low doses to the biological system.

The filter memory can be programmed with not only what type of alarm should be activated when these conditions occur but also the alarm limits that will cause the alarms to be initiated. This can allow very sensitive biological systems that need very tight dosing specifications to have tight alarm initiating limits and those that only require loose limits can have them set accordingly.

Yet another set of parameters that can be programmed into the filter memory are what user adjustable settings may be active on the nitric oxide generating apparatus user interface. For instance some biological systems may require the dose to be slowly reduced over time as the biological system responds to treatment, or depending on the size of the biological system, the gas flow rate through the chamber may need to be adjusted for the different system size. In another option, it may be advantageous to allow the user to set the alarm limits for the gas flow or the nitric oxide concentration. The description in this specification of the possible parameters that can be stored in the filter memory for a given custom biological system application is not meant to be exhaustive but allows the concept of custom parameters to be described.

These figures will now be described in more detail.

DETAILED DESCRIPTION OF THE INVENTION

In the following detailed description the term "air" will be used to generally describe the oxygen and nitrogen gas mixture used in reactor chamber to generate nitric oxide, but also other gas mixtures containing oxygen and nitrogen that may have been produced from alternative gas sources such gas cylinders that are commonly used in anesthesia machines and may include alternate concentrations.

Figure 1:
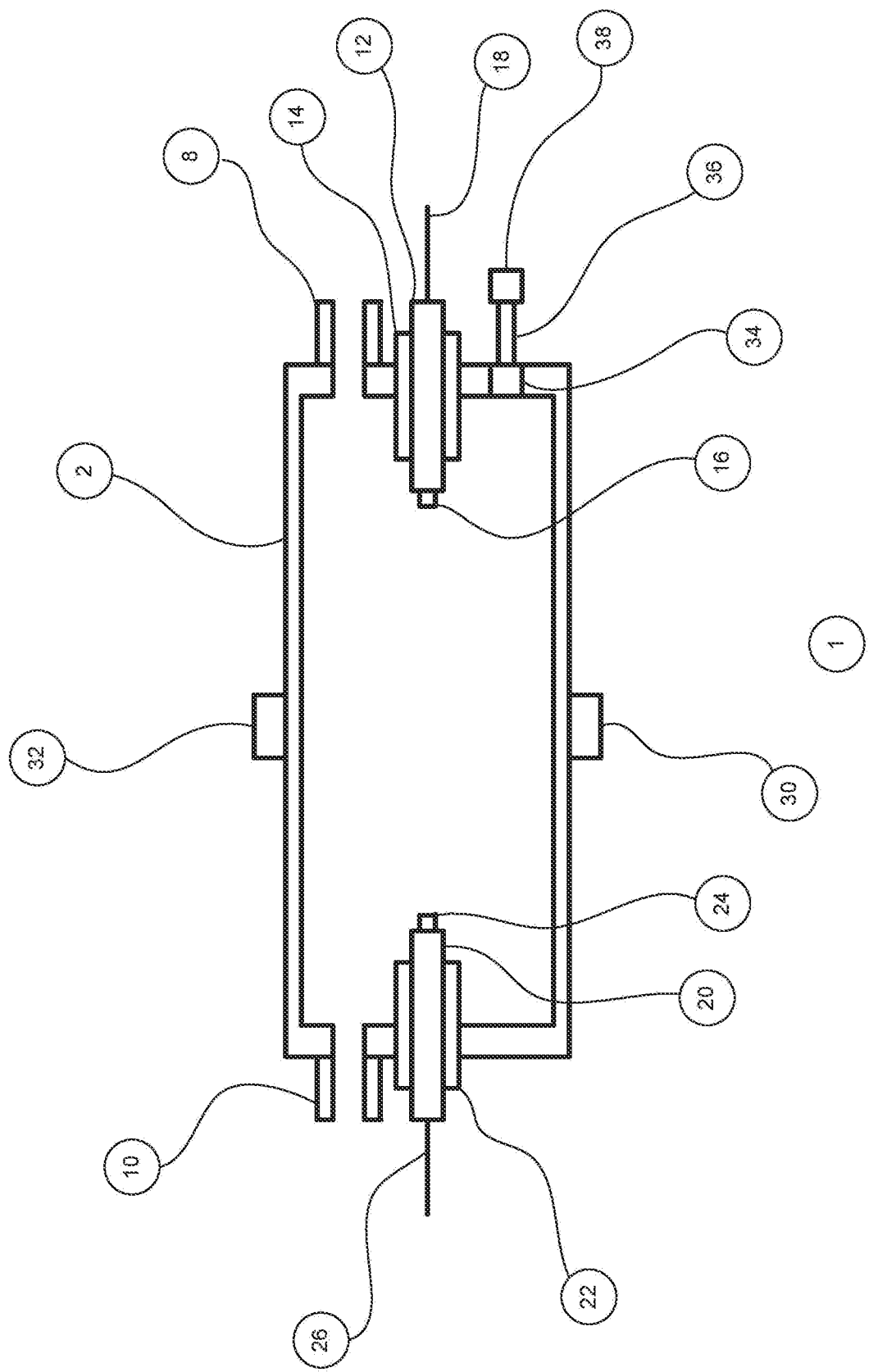
FIG. 1 is a cross-sectional view of the reactor chamber showing the main components of the reactor chamber design.

FIG. 1 shows the nitric oxide reactor chamber 1 with a reactor housing 2 which has a reactor gas inlet port 8 and a first electrode 12 on one side and a reactor gas outlet port 10 and a second electrode 20 on the other side. The electrodes can be insulated with non-electrically conducting material 14 and 22 if the chamber housing is made of a material that is electrically conducting. The electrodes can have an electrode tip 16 and 24 made of a material that is resistant to high temperatures and is less susceptible to vaporization, oxidization and wear. Materials for the electrode tips can be selected from the Nobel metal group of the periodic table that includes tungsten and platinum. The electrodes are connected to the electronic control circuit with the insulated electrical cables 18 and 26.

Figure 5:
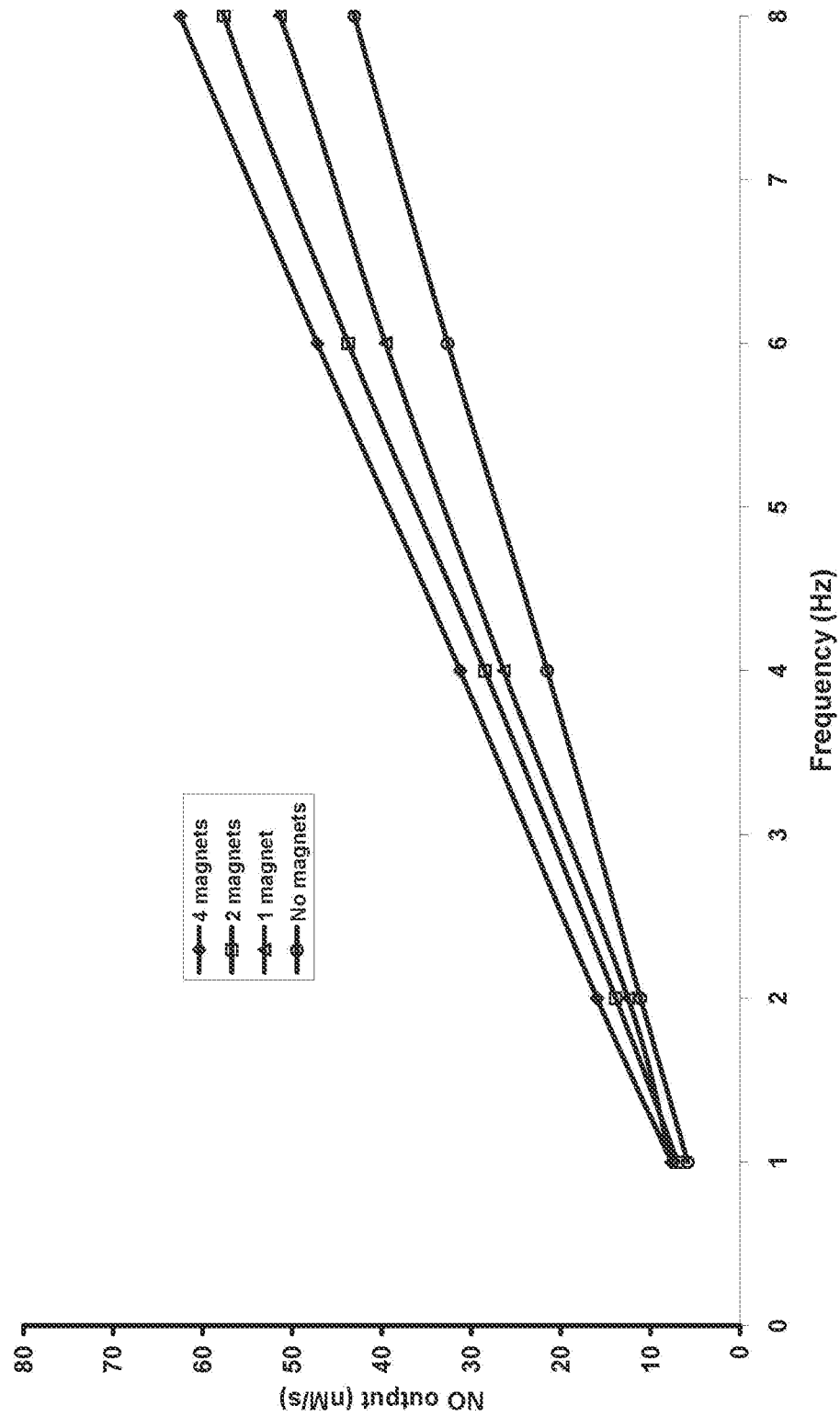
FIG. 5 is a graph that illustrates the improved generation of nitric oxide when a magnetic field is used in the design.

In one embodiment of the invention the reactor chamber can have magnets 30 and 32 located on the reactor housing 2 so they are adjacent to the air gap between the electrodes 12 and 20, each magnet with the opposite pole facing the chamber so they reinforce the magnetic field across the air gap. One embodiment of the invention has a magnet on each side of the air gap although a single stronger magnet that exerts the same magnetic field strength across the air gap is equally applicable. The magnetic field across the air gap is believed to cause dispersal of the electrical discharges across the air gap, which results in a larger plasma cross-sectional area and more efficient generation of nitric oxide. In one embodiment the magnets are rare earth magnets made from neodymium iron and boron. In testing, the addition of magnets resulted in approximately 45% more nitric oxide being generated for exactly the same pulse discharge settings as without magnets (FIG. 5).

The reactor housing 2 can have a port 34 that allows a photodiode 38 to be in optical communication with the inside of the reactor chamber 1. The optical communication can be provided so the photodiode is mounted directly to the port 34 in the reactor housing or more preferably a fiber optic cable 36 is mounted to the reactor chamber port and then to the photodiode so said photodiode can be located away from the reactor chamber and the electrical disturbances cause by the pulse electric discharges. The photodiode 38 provides a signal that is proportional to the light energy falling on its active surface. When the pulsed electric discharges occur, light is generated in the ionized plasma and the photodiode detects this light. The light signal from the photodiode occurs at the same frequency and pulse duration as the electric discharge as long as the discharge takes place.

Figure 2:
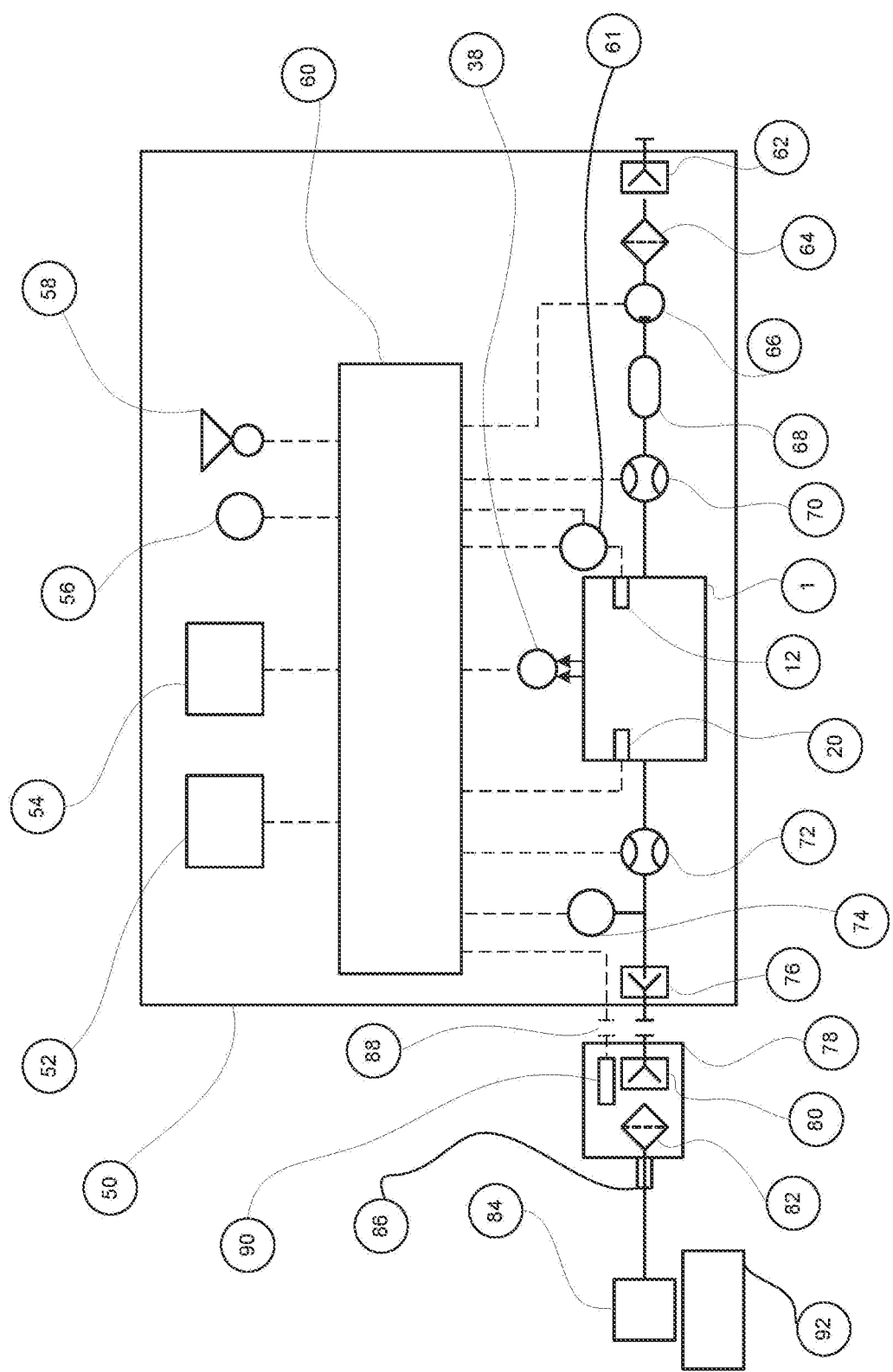
FIG. 2 is a schematic diagram of the nitric oxide generator showing the components of the system and their electrical and pneumatic connections.

FIG. 2 is a schematic diagram of the nitric oxide generator. There are three main subsystems that make up the nitric oxide generator, the nitric oxide generator unit 50, the outlet filter assembly 78 and the nitric oxide applicator 84. The nitric oxide generator unit is where the nitric oxide is generated in controlled amounts and where it is delivered to the generator gas outlet port 76. The generator unit 50 has a main electronic control circuit 60 that interfaces to the main electrical components of the system and provides the main system control features. In one embodiment of the invention this is a microprocessor based control circuit executing a stored program held in a non transitory medium, but it is not intended to limit the invention only to microprocessor based control circuits, analog circuits could also be used. Attached to the electronic control circuit are the main user controls comprising of an input setting unit 52 a visual display unit 54, a visual alarm indicator 56 and an audible alarm sounder 58, these components are used to provide the desired settings to the main control, display any preprogrammed settings that may have been automatically set from the preprogrammed filter memory and provide audible and visual alarms when there are fault conditions. The main components in contact with the air flow though the device are, the generator gas inlet 62 where the air is drawn into the unit, the inlet filter 64 which is used to filter the air and remove any unwanted contaminants, the air pump 66 is used to draw the air in from the gas inlet port 62 and to adjust the amount of air flow that is passed through the reactor chamber 1 under the control of the electronic control circuit 60. If the air pump 66 provides un-calibrated control of the gas flow, a gas flow meter 70 can be used to provide the electronic control circuit an accurate indication of the gas flow so the pump can be finely adjusted by the electronic control circuit 60 until the gas flow is at the desired set value. If the gas pump 66 provides oscillatory gas flow output as in the case of a piston pump then a damping chamber 68 can be provided to smooth out the oscillations. The gas flow then passes through the reaction chamber 1 where the electric control circuit 60 controls the frequency and duration of the electric discharges across the electrodes 12 and 20 such that nitric oxide is generated in the air passing through the chamber. The gas leaving the reaction chamber 1 passes through a second flow meter 72, which is used by the electronic control circuit to provide an independent check that the flow through the reaction chamber is correct. If there has been a failure in the gas pump 66 (indicated by a zero flow rate) or the first flow meter 70 or 72 (indicated by different readings between flow meter 70 and flow meter 72) such that the gas flow through the reaction chamber is not correct, then the electronic control circuit can initiate a visual and/or audible alarm to alert the user to the failure. To detect if there has been a failure in the electric discharge circuits there is the photodiode 38 and/or the electrode current and/or voltage sensing circuit 61 that are connected to the electronic control circuit 60, which can determine if the right frequency and pulse duration has been achieved. After the outlet gas flow meter 72 there is an optional pressure trigger sensor 74 connected to the gas flow conduit 73. This pressure trigger sensor 74 can be used by the electronic control circuit 60 to control the nitric oxide delivery as a bolus (when the pressure trigger sensor is activated) rather than as a known concentration in a continuous gas flow rate of air. The different modes of delivery will be described in more detail later in the specification. The gas flow continues past the pressure trigger sensor 74 to the gas outlet port 76, where it connects to the outlet filter assembly 78 and out through the nitric oxide applicator 84, where it is applied to the biological system 92.

The outlet filter assembly 78 has an inlet filter port 80, which connects to the gas outlet port of the nitric oxide generator unit 50, a chamber containing adulterant filter material 82, and an outlet port 86, which connects to the nitric oxide applicator 84. Adulterant filter materials include materials such as soda lime, activated charcoal, activated alumina and silica gel soaked in ascorbic acid. These materials and others known in the art to remove $NO_2$ from gases containing nitric oxide while leaving the nitric oxide levels substantially unchanged may be used.

Such materials may have a fixed capacity for removing or converting $NO_2$ before there effectiveness is consumed and they therefore require replacing after a period of use. The size of the filter and the amount of $NO_2$ they are exposed to will impact the usage time before they need replacing. The filter assembly 78 in addition includes a readable programmable memory 90, which connects to the nitric oxide generator unit through a filter electrical connection 88. The other side of connector 88 connects to the electrical control circuit 60 where the readable programmable memory 90 can be read and reprogrammed by the electrical control circuit 60 as the filter is consumed. One embodiment of the readable programmable memory is an EEPROM, which has a serial interface for reading and programming the memory. An alternative embodiment is where each individual EEPROM (and hence filter assembly) has its own unique identifier included in a small amount of read only memory (ROM). An example of this type of memory is part number 24AA02E48T from Microchip Technology, this is a 2 KBIT EEPROM with each memory chip having its own MAC address permanently programmed into a small section of read only memory. This type of EEPROM with its unique identifier programmed into ROM means that no two filter assemblies will have the same identifier and the identifier will not be able to be updated during use as can occur with the data in the EEPROM memory. This can provide additional protection against reusing spent filters, as individual filter identifiers can be stored in the nitric oxide generator when they are used and then the generator will prevent filters with the same identifiers being used in the future for example, as might occur if the EEPROM usage data were improperly altered by a corrupted system. An alternative embodiment is where a micro-controller with embedded EEPROM and FLASH memory is used instead of just a serial memory device. This embodiment has the advantage that the reprogramming of the memory can be performed locally by the micro-controller and reduce the processing overhead of the electronic control circuit 60. An example of this type of micro-controller is the ATtiny25/45/85 from Atmel.

Generally the EEPROM, may store usage information obtained from the electronic control circuit 60 that reveals the historical concentrations of NO being produced and thus the likely exhaustion rate of the filter 82. Thus, when the filter 82 is used for high NO concentrations and/or high flow rates this will be recorded and the user instructed to replace the filter more frequently than if the filter 82 is used for low NO concentration and/or low flow rate applications. This exhaustion information may be derived both from the concentration value determined by the electronic control 60 and the flow rates determined from flow sensors 72 and 70. The EEPROM may also include a proprietary code indicating that it is authorized equipment preventing spoofing of the apparatus with devices that may not provide the desired filtering. The proprietary code may, for example, use any number of techniques including public-key encryption techniques that prevent easy duplication of spurious codes.

Figure 3:
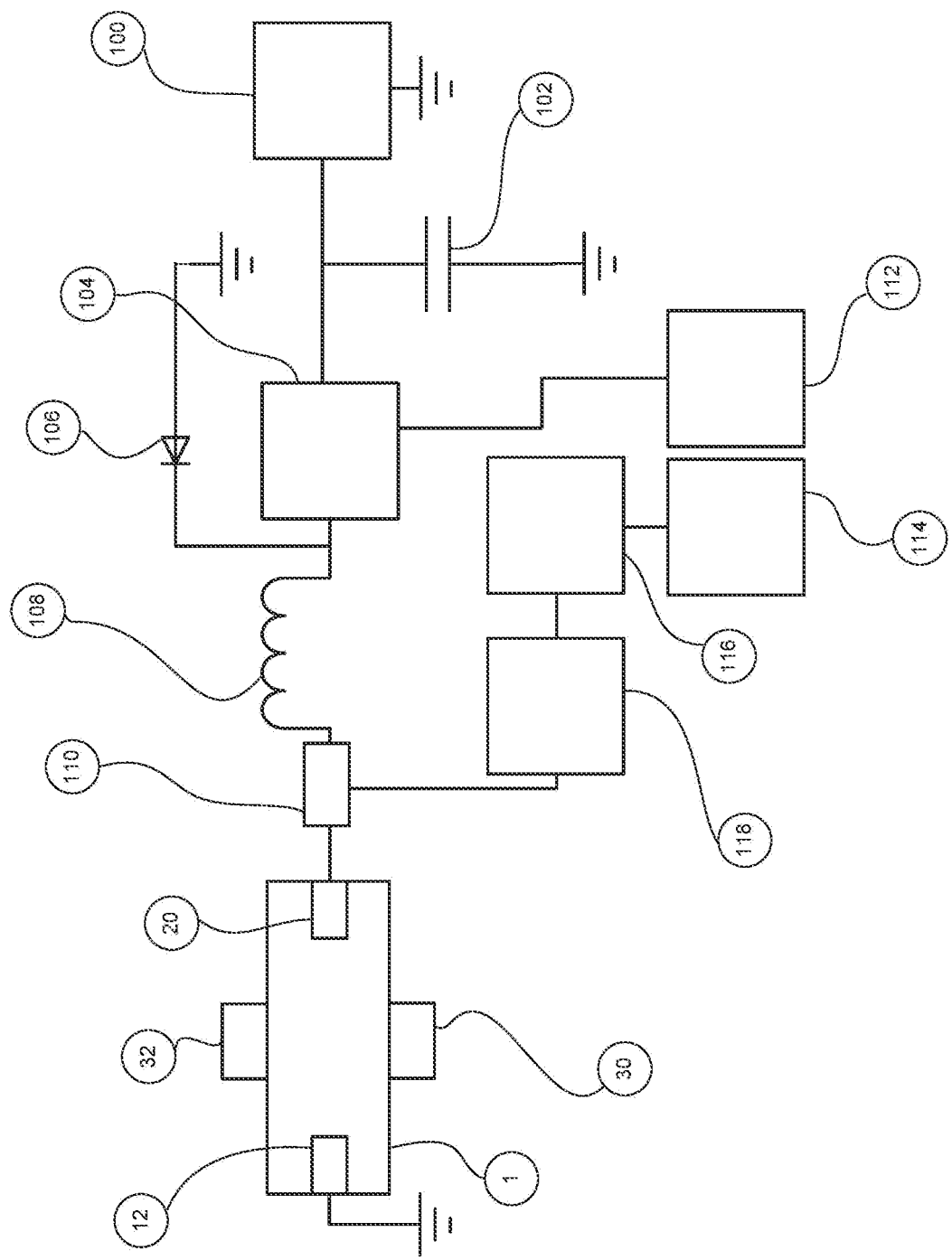
FIG. 3 is an electronic schematic of the pulsed electric discharge drive circuit.

FIG. 3 shows a schematic of the electric discharge drive circuit that is part of the electronic control circuit 60. This represents one embodiment of the drive circuit and people of ordinary skill in the art will appreciate there are other circuit possibilities that can achieve the same function. To establish the high voltage required to initially ionize the air between the electrodes 12 and 20, a capacitor discharge circuit 116 discharges current through a transformer 118 when triggered by a pulse trigger controller 114. This results in a high voltage on the other side of the transformer 118 which is sufficient to cause dielectric breakdown and ionize the gas and initiate current across the electrodes 12 and 20. The discharge pulse duration is maintained by a second circuit, which is powered by a high voltage DC power supply 100. In the case that the instantaneous current draw is high, the DC power supply 100 is buffered by a capacitor 102 to smooth out any high current fluctuations. The DC voltage and current is controlled on or off by a transistor 104 that is controlled by a pulse duration control circuit 112 which controls the pulse duration by controlling the on time of the transistor. The drive circuit functions as follows, the electronic control circuit 60 calculates the desired electric discharge frequency and pulse duration that will generate the desired quantity of nitric oxide, it then triggers each discharge with the pulse trigger controller 114 which causes a quick high voltage pulse from the transformer 118, at the same time the electronic control circuit turns on the transistor 104 for the desired pulse duration with the pulse duration control circuit 112. The resulting pulse discharge voltage across the electrodes is the desired initial high voltage spike to ionize the gas between the electrodes followed by the desired lower voltage and current for maintaining the desired pulse duration. The actual voltage and current can be controlled by the electronic control circuit 60 if the pulse duration control circuit 112 works in a pulse width modulation (PWM) mode during the on phase of the pulse discharge. If this PWM mode is used it is desirable to use an inductor 108 to smooth out the modulated current during the electric discharge pulse. The interface circuit 110 joins the two control circuits prior to applying the discharge voltage to the electrode. It is desirable that this interface circuit 110 use high voltage diodes to prevent the high voltage spikes from the pulse transformer damaging the transistor 104. The diode 106 provides an additional mechanism that grounds any high voltage spike greater than its breakdown voltage or negative transients from getting to the pulse duration control circuit 112. It can be appreciated that this circuit provides a great deal of flexibility in controlling not only the pulse frequency and the pulse duration but also the voltage and current levels during the pulse duration phase of the electric discharge. This allows the electronic control circuit to optimize the electric discharge frequency and pulse duration settings to maximize the effectiveness at generating the desired quantity of nitric oxide while at the same time minimizing the electric discharge current and so reducing the gas temperature and the electrode wear.

Figure 4:
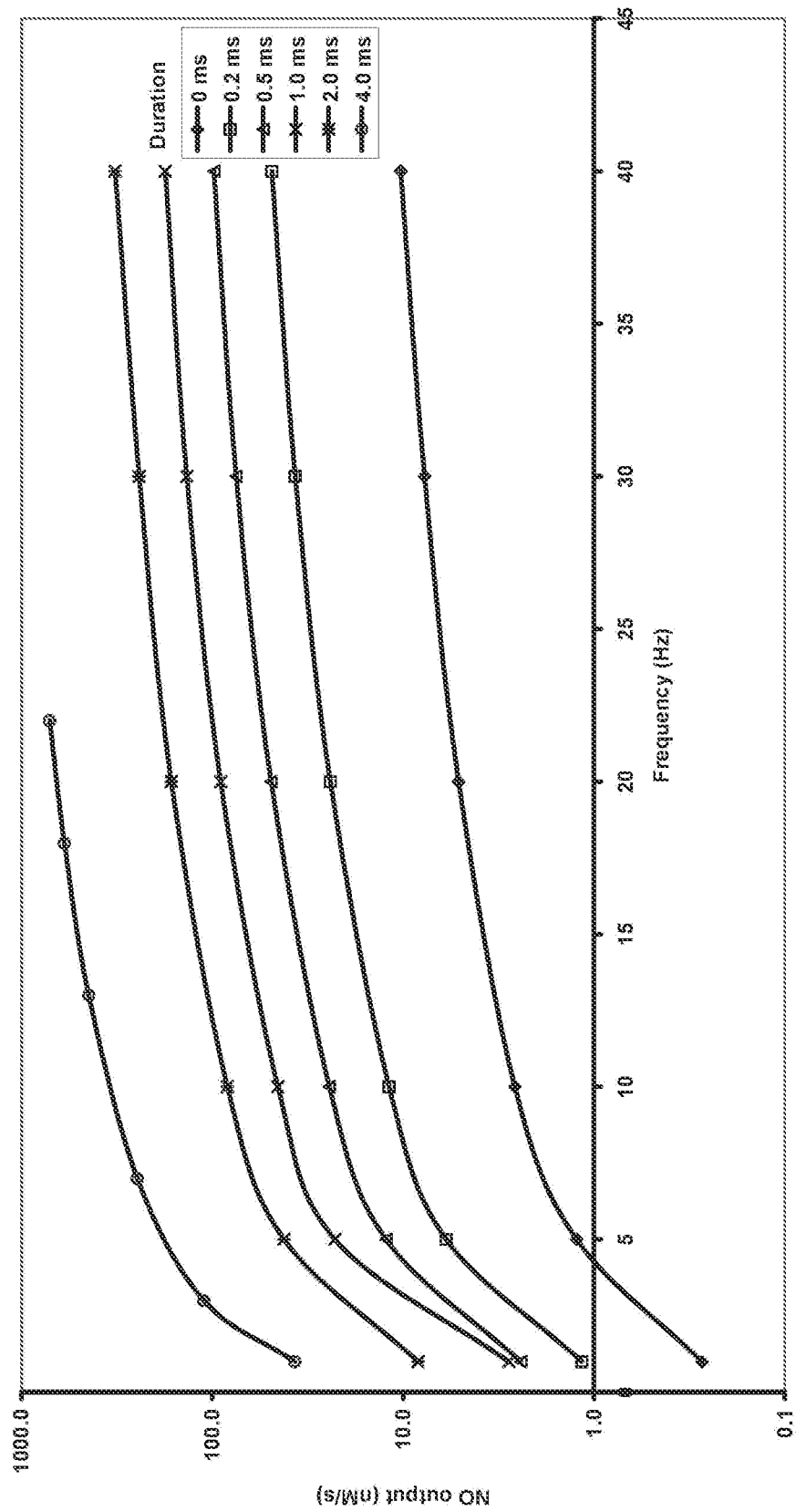
FIG. 4 is a graph that illustrates the wide performance range of the system with the amount of nitric oxide being generated varying from 0.27 to 711 nanamoles/second nM/s.

The pulses of electric discharge can be controlled over a wide range depending on the nitric oxide requirements; a frequency range of 0.1 to 100 Hz with the pulse duration range between 0.1 to 10 milliseconds (ms) has been demonstrated. FIG. 4 shows a graph of nitric oxide output in nM/s against the discharge frequency (Hz) for different pulse duration intervals from 0 up to 4 ms. It shows nitric oxide being generated from 0.27 nM/s at 1 Hz and zero injection up to 711 MVPs at 22 Hz and 4 ms of injection. This example was where the high voltage DC power supply was at 1,000 volts and the pulse duration control circuit operated in PWM mode so that the current across the electrodes was approximately 60 mA. These parameters can be programmed into the electronic control circuit, for example in a lookup table, so based on the required rate of nitric oxide generation, the correct frequency, duration and PWM control can be used. The values in the lookup table which map desired concentration to the correct frequency and duration of the arc may be determined empirically. In practice this means that nitric oxide concentrations can be generated and controlled over the wide range of concentrations of 1 to 1000 ppm in a flow rate in the range of 0.5 to 2 L/min depending on the requirement of the biological system being treated.

A further improvement of at least one embodiment of the invention is the use of a magnetic field to increase the amount of nitric oxide generated by the apparatus. FIG. 5 shows a graph of the nitric oxide output from the apparatus in nM/s versus discharge frequency (Hz) for different magnetic fields. The parameters used for these tests were exactly the same (PWM was set for electrode voltage 120V at a current 400 mA), with the only difference being the number of magnets adjacent to the electrode gap. As can be seen the nitric oxide output increases by approximately 45% when four ½" diameter rare earth magnets, two on each side of the chamber housing, are used in the design compared to no magnets. It is clear from FIG. 5 that as the number of magnets (and hence the magnetic field) increase, the amount of nitric oxide being generated also increases.

The mode of operation will have some differences depending on the type of biological system and what kind of dosing is required. There may be some modes where the gas flow through the system is at a constant flow rate and a constant concentration of nitric oxide for the application is required. In others a bolus mode of delivering the gas flow to the biological system may be desired so an intermittent known quantity of nitric oxide is required, for example nM/pulse. The intent is to be flexible so as to cover all the main permutations of these delivery modes and how this is achieved is covered in the following.

In general the electronic control circuit 60 gets the desired setting for the nitric oxide dose from the user setting unit 52, the readable programmable memory 90 on the filter assembly 78 or if it is a nitric oxide generator that is only configured for one specific application with one dosing level then from the electronic control circuit's 60 internal memory. The dose setting selected can be displayed on the display unit 54 so the user knows the dose level that is to be delivered.

The dose setting can be in different units depending on the mode of delivery, it can be set as a concentration such as parts per million (ppm) or micro liters per liter (uL/L), or it can be set as a quantity per unit of time such as nanomoles per second (nM/s) or nanomoles per minute (nM/min) or it can also be in terms of a quantity of nitric oxide to be delivered per event which will be described later in the specification. The dose setting entered into the electronic control circuit 60 determines the required pulse frequency and pulse duration of the electric discharge to produce nitric oxide at the required rate.

If the dose setting was set as a concentration of nitric oxide at a desired airflow rate Q then the amount of nitric oxide in nM/s required to be generated in the gas flow can be calculated by equation 1.

$$rNO = (Q/60) \cdot (C_{NO} * 1000) / Vm \qquad \text{Equation 1}$$

Where rNO is the rate of nitric oxide production nM/s
Q is the gas flow rate (L/min)
$C_{NO}$ is the concentration of nitric oxide (ppm)
Vm is the mole volume (approx 24.8 L/M at 25° C. 1 atm)

Once the rate of nitric oxide (rNO) has been calculated from the input settings, the required electric discharge frequency and pulse duration can be determined by the electronic control circuit using the previously determined relationship between the parameters (example FIG. 4) as enrolled in a lookup table in computer memory or implemented algorithmically by an equation in computer memory. The required gas flow rate (Q) through the chamber is delivered from the gas pump 66 under the control of the electronic control circuit 60. The flow meter 70 provides a signal proportional to the gas flow to the electronic control circuit 60, which adjusts the gas pump control until the desired gas flow is achieved. The use of an air pump to provide the gas flow through the chamber is not the only means to provide the gas flow and it is being used as an example. For instance if the air supply was from a pressurize pipeline or a gas cylinder then a control valve could be used to control the flow of gas instead of the air pump. Also, if it was required to add nitric oxide into an air flow stream that was being controlled by another external device, then no control valve or air pump would be required, in this case the gas flow meter 70 would be used to provide the electronic control circuit with the measurement of the air flow rate so the rate of nitric oxide generation can be determined. If the external flow control device has means to electronically communicate the gas flow measurement to the electronic control circuit then even the gas flow meter 70 is not needed for the correct functioning of the apparatus. With the desired gas flow rate established and the required electric discharge frequency and pulse duration determined the electronic control circuit 60 can initiate electric discharges across the electrodes 12 and 20 and the nitric oxide containing gas will flow out through the gas outlet port 76.

When in the bolus mode of oxide delivery, the input setting unit 52 will be used to enter the nitric oxide as a known quantity of nitric oxide in units such as nano-moles (nM) or micrograms (μg) and also the volume of the gas to deliver the nitric oxide to the biological system. The electronic control circuit will determine the number and the duration of electric discharges required to produce that quantity of nitric oxide, and the bolus of nitric oxide will be generated and delivered when the pressure trigger sensor 74 is activated. One embodiment of the pressure trigger sensor 74 is a pressure transducer with an adjustable limit to set the level that the trigger is activated. The pressure transducer can measure both positive and negative pressure relative to ambient and the trigger to initiate the bolus delivery can also be a positive or negative pressure.

Figure 6:
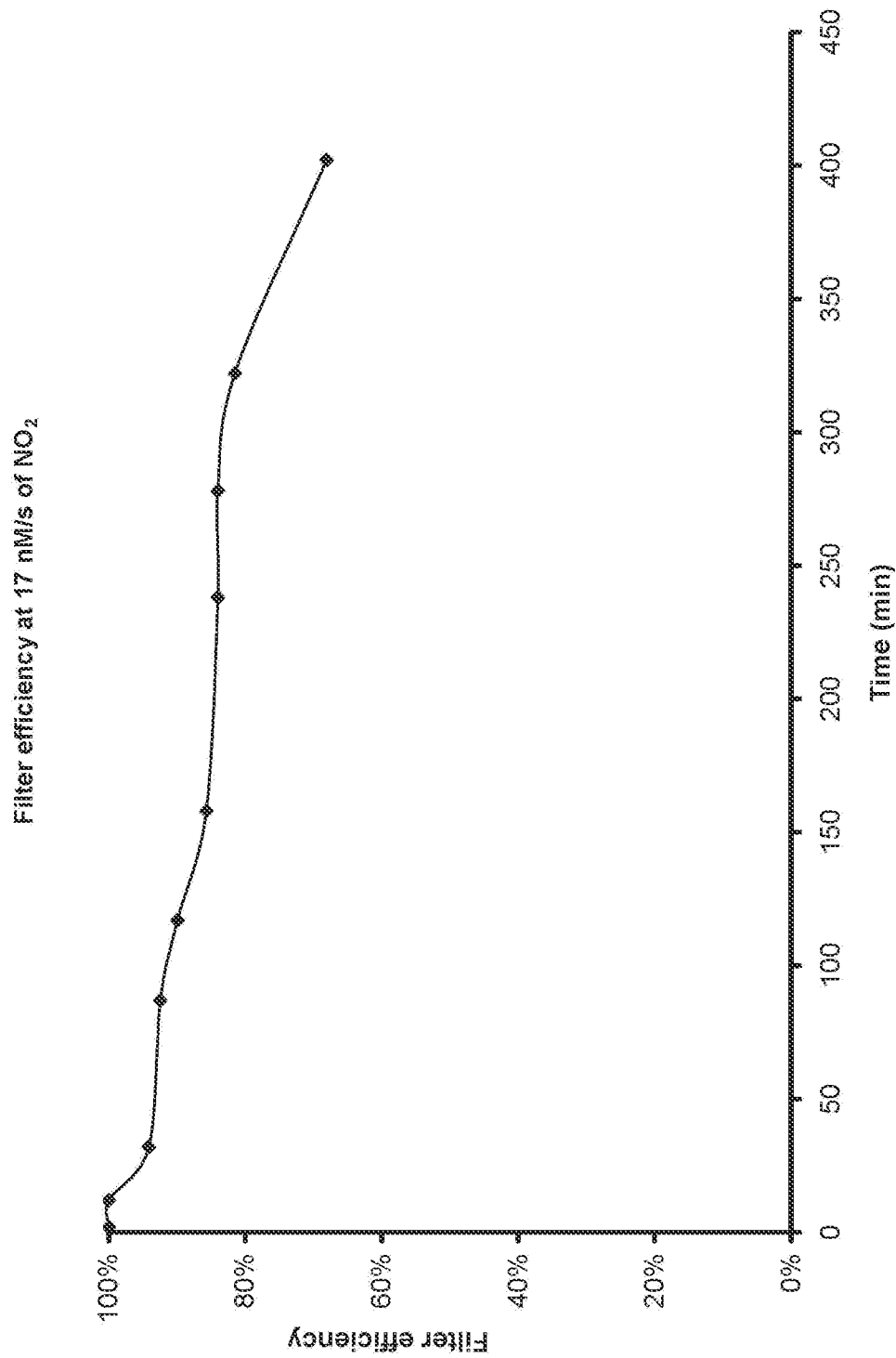
FIG. 6 is a graph that illustrates the removal of $NO_2$ by a filter.

For example, delivering nitric oxide to a cystic fibrosis patient where the application is to combat their lung infection. If the patient is breathing spontaneously and the nitric oxide applicator is a nasal cannula connected to the patient's nose, then as the patient breathes in, the pressure in the nitric oxide applicator will go negative relative to ambient and the pressure trigger sensor would need a negative pressure trigger setting to trigger the bolus so it goes to the patients lung during inspiration. However, if the patient is on a positive pressure ventilator which has positive pressure in the breathing circuit during inspiration, then the trigger setting limit would require a positive pressure setting to trigger the bolus during inspiration. When the pressure trigger sensor 74 is activated, the electronic control circuit 60 initiates the electric discharge pulses required to generate the nitric oxide set on the input setting unit 52 and in addition the gas pump 66 is turned on to deliver the desired volume of gas set by the input setting unit 52 or programmable memory 90, once the volume of gas has been delivered the gas pump is turned off again. In this way a bolus of gas is delivered to the biological system each time the pressure trigger sensor 74 is activated and the bolus of gas contains the desired set quantity of nitric oxide. In the case of a patient breathing normally in and out, the bolus of nitric oxide gas could be delivered to the patient at each breath. The nitric oxide gas leaves the nitric oxide generating unit at the gas outlet port 76 and goes through the outlet filter assembly 78. The filter assembly 78 is attached to the outlet port 76 and the gas will flow through the filter 82 where adulterants such as nitrogen dioxide ($NO_2$) are removed. As an example of the effective performance of a filter in removing adulterant's an activated charcoal filter with 0.54 grams of material was assembled into a filter housing, the gas concentration of nitric oxide and nitrogen dioxide were analyzed over time before and after the filter assembly. The conditions for the filter performance testing were 225 ppm of nitric oxide at 2 L/min with 12 ppm of nitrogen dioxide in the gas mixture. FIG. 6 shows a graph of the filter efficiency over time, efficiency being defined as the percent of nitrogen dioxide in the gas being removed. The filter efficiency remained over 80% after 300 minutes of continuous use under these test conditions.

After the filter, the nitric oxide gas flow passes into the nitric oxide applicator 84, which conducts and applies the nitric oxide to the biological system 92. There is a wide range of designs of nitric oxide applicators that can be tailored for the wide range of potential applications in a wide range of biological systems. A few of the different types of nitric oxide applicator will be described to provide examples of the different types of applications that can be supported by the nitric oxide generation device:

A piece of tubing, with a diffuser on the distal end that directs the nitric oxide gas flow directly to the surface of the biological system. An example is a tube with a diffuser to apply nitric oxide to a non-healing wound such as a diabetic ulcer.

A simple tube that connects to a chamber with the biological system present. Examples include a chamber that holds dormant wheat seeds that can be brought out of dormancy by exposure to nitric oxide or the chamber may be a sterilizing chamber where articles that are contaminated with bacterial or fungus can be sterilized by exposure to nitric oxide.

A tube with a squeeze bulb in series that connects via a probe into a chamber, which contains the biological system. The probe is connected to the package and the bulb is squeezed which triggers the pressure trigger sensor in the device to deliver a bolus of nitric oxide gas in to the package. Example, the chamber could be a gas tight plastic bag that holds a modified atmosphere to ship cut flowers (e.g. tulips) and extend the life of the product during shipping.

A tube connecting to a nasal cannula or a face mask that attaches to a patients nose/mouth to treat a patient with a lung infection such as occurs in cystic fibrosis. The gas flows from the nitric oxide applicator could be continuous flow at a set concentration or it could be pulsed as a bolus when the patient breathes in or out and triggers the pressure trigger to deliver the bolus.

A tube that connects to a ventilator breathing system attached to a patient with a lung infection that triggers a bolus of nitric oxide when the pressure in the circuit increases during inspiration and triggers a bolus delivery of nitric oxide.

These examples are not meant to include a comprehensive list of all possible nitric oxide applicators but to give a general view of the wide potential of applications the nitric oxide generation apparatus can be used for.

We claim:
1. A method for generating nitric oxide comprising:
    (i) providing a flow of a reactant gas comprising nitrogen and oxygen to an apparatus comprising:
        (a) a reaction chamber;
        (b) an inlet to provide the flow of the reactant gas comprising nitrogen and oxygen to the reaction chamber;
        (c) a pair of electrodes in the reaction chamber and separated by a gap;
        (d) an electronic control circuit in communication with the electrodes to generate an electric arc discharge across the gap, wherein the electronic control circuit is configured to control a pulse frequency of the electric arc discharge and a pulse duration of the electric arc discharge independent of the pulse frequency;
        (e) an outlet for a product gas comprising nitric oxide;
    (ii) promoting the electric arc discharge across the electrodes through the gas flow while controlling the pulse frequency of the electric arc discharge and the pulse duration of the electric arc discharge to produce the product gas comprising nitric oxide; and
    (iii) outputting the product gas comprising nitric oxide.

2. The method of claim 1, wherein the electronic control circuit is configured to provide a constant current during the electric discharge.

3. The method of claim 1, wherein the product gas comprising nitric oxide is generated using a flow of the reactant gas through the reaction chamber.

4. The method of claim 3, wherein the apparatus further comprises a flow device to provide the flow of the reactant gas through the reaction chamber.

5. The method of claim 4, wherein the flow device is selected from the group consisting of: a flow sensor for measuring the gas flow from an external regulated source to produce the gas flow, a pump system operating to produce the gas flow without flow sensing, a control valve, and a pump system with a flow sensor system providing feedback control of the pump system to produce the gas flow.

6. The method of claim 4, wherein the flow device is positioned between the inlet and the reaction chamber.

7. The method of claim 4, wherein the flow device is configured to provide the flow of the reactant gas based on a measurement associated with a medical gas into which the product gas flows.

8. The method of claim 7, wherein the measurement associated with the medical gas is a flow rate of the medical gas such that the flow of the reactant gas through the reaction chamber is proportional to the flow rate of the medical gas.

9. The method of claim 1, wherein the apparatus further comprises one or more filters.

10. The method of claim 9, wherein at least one of the one or more filters is arranged upstream of the reaction chamber.

11. The method of claim 9, wherein at least one of the one or more filters is arranged downstream of the reaction chamber and is configured to remove $NO_2$ from the product gas.

12. The method of claim 1, wherein the apparatus further comprises one or more sensors.

13. The method of claim 12, wherein at least one of the one or more sensors is a pressure trigger sensor.

14. The method of claim 12, wherein at least one of the one or more sensors is a flow sensor.

15. The method of claim 12, wherein at least one of the one or more sensors is a discharge sensor.

16. The method of claim 1, wherein the electronic control circuit is further configured to generate an electric arc discharge across the gap in response to detecting inspiration.

17. The method of claim 1, wherein the apparatus further comprises a transformer in communication with the electronic control circuit.

18. The method of claim 1, wherein the outlet is in communication with a nitric oxide applicator to deliver the product gas to a patient.

19. The method of claim 18, wherein the nitric oxide applicator is selected from a group consisting of a nasal cannula, a face mask, and a tube in communication with a ventilator breathing system.

20. The method of claim 1, wherein the apparatus is configured to be used with a ventilator.

21. The method of claim 1, wherein the apparatus further comprises a capacitor discharge circuit.

22. The method of claim 1, wherein the apparatus further comprises a pulse duration control circuit.

23. The method of claim 22, wherein the pulse duration control circuit comprises a transistor.

24. The method of claim 23, wherein the transistor comprises a high voltage diode.

25. The method of claim 23, wherein the pulse duration control circuit controls the transistor in a pulse width modulation mode to control an average current during pulse duration phase of the electric discharge.

26. The method of claim 23, wherein the electronic control circuit comprises an inductor to smooth a pulse width modulated current from the transistor.

27. The method of claim 1, where the electronic control circuit is configured to control the pulse frequency of the electric arc discharge to within a range of 0.1 and 100 Hz, and the pulse duration of the electric arc discharge to within a range of 20 microseconds and 500 milliseconds.

28. The method of claim 1, wherein the apparatus further comprises a pulse trigger controller.

29. A method for generating nitric oxide comprising:
(i) providing a flow of a reactant gas comprising nitrogen and oxygen to an apparatus comprising:
   (a) a reaction chamber;
   (b) an inlet to provide the flow of the reactant gas comprising nitrogen and oxygen to the reaction chamber;
   (c) a pair of electrodes located in the reaction chamber and separated by a gap;
   (d) an electronic control circuit in communication with the electrodes to generate an electric arc discharge across the gap, wherein the electronic control circuit is configured to control a pulse frequency of the electric arc discharge and a pulse duration of the electric arc discharge independent of the pulse frequency; wherein the pulse frequency of the electric arc discharge is within a range of 0.1 and 100 Hz, and the pulse duration of the electric arc discharge is within a range of 20 microseconds and 500 milliseconds,
   (e) one or more sensors;
   (f) one or more filters; and
   (g) an outlet for a product gas comprising nitric oxide;
(ii) promoting the electric arc discharge across the electrodes through the gas flow while controlling the pulse frequency of the electric arc discharge and the pulse duration of the electric arc discharge to produce the product gas comprising nitric oxide; and
(iii) outputting the product gas comprising nitric oxide.

30. The method of claim 27, where the electronic control circuit is configured to control the pulse frequency of the electric arc discharge to within a range of 0.1 and 45 Hz, and the pulse duration of the electric arc discharge to within a range of 0.1 milliseconds and 10 milliseconds.

31. The method of claim 29, where the electronic control circuit is configured to control the pulse frequency of the electric arc discharge to within a range of 0.1 and 45 Hz, and the pulse duration of the electric arc discharge to within a range of 0.1 milliseconds and 10 milliseconds.

32. The method of claim 1, where the electronic control circuit is configured to further control an average current during the electric arc discharge to within a range of 20 to 3000 milliamps.

33. The method of claim 29, where the electronic control circuit is configured to further control an average current during the electric arc discharge to within a range of 20 to 3000 milliamps.

* * * * *